US010016733B2

(12) United States Patent
Shen et al.

(10) Patent No.: US 10,016,733 B2
(45) Date of Patent: *Jul. 10, 2018

(54) ANIONIC SURFACTANT COMPOSITIONS AND USE THEREOF (71) Applicant: Dow Global Technologies LLC, Midland, MI (US)

(72) Inventors: Cheng Shen, Shanghai (CN); Jianhai Mu, Shanghai (CN); Xiaohua Wang, Shanghai (CN)

(73) Assignee: Dow Global Technologies LLC, Midland, MI (US)

( * ) Notice: Subject to any disclaimer, the term of this patent is extended or adjusted under 35 U.S.C. 154(b) by 435 days.

This patent is subject to a terminal disclaimer.

(21) Appl. No.: 14/424,068

(22) PCT Filed: Sep. 29, 2012

(86) PCT No.: PCT/CN2012/082444
§ 371 (c)(1),
(2) Date: Feb. 26, 2015

(87) PCT Pub. No.: WO2014/047924
PCT Pub. Date: Apr. 3, 2014

(65) Prior Publication Data
US 2015/0224462 A1   Aug. 13, 2015

(51) Int. Cl.
*B01J 13/00* (2006.01)
*B01F 17/00* (2006.01)
(Continued)

(52) U.S. Cl.
CPC ...... *B01F 17/0092* (2013.01); *B01F 17/0057* (2013.01); *C07C 309/68* (2013.01);
(Continued)

(58) Field of Classification Search
CPC .... B01F 17/0092; B01F 17/0057; C08F 2/26; C08F 2/30; C07C 309/68; C08G 65/326;
(Continued)

(56) References Cited

U.S. PATENT DOCUMENTS 3,120,505 A   2/1964   McCubbin et al.
3,317,495 A   5/1967   Jones et al.
(Continued)

FOREIGN PATENT DOCUMENTS

CN   1266065   3/2005
CN   101584974   11/2009
(Continued)

OTHER PUBLICATIONS

Derwent Abstract, week 201710, London: Derwent Publications Ltd., AN 2014-R06848, Class A60, U.S. Pat. No. 9555385 B2, (Dow Global Technologies Inc), abstract.*
(Continued)

*Primary Examiner* — Daniel S Metzmaier
(74) *Attorney, Agent, or Firm* — Brooks, Cameron & Huebsch, PLLC (57) ABSTRACT Provided are surfactant compositions that are useful as alternatives to alkylphenol ethoxylates (APEs) type surfactants in emulsion polymerization. The surfactant compositions comprise: an alkyl alkoxylate sulfate of formula (I): $R^1O\text{—}(CH_2CH(R^2)\text{—}O)_x\text{—}(CH_2CH_2O)_y\text{—}SO_3M$ wherein $R^1$, $R^2$, x, y, and M are as defined herein.

8 Claims, 4 Drawing Sheets (51) Int. Cl.
*C08F 2/26* (2006.01)
*C08F 2/30* (2006.01)
*C07C 309/68* (2006.01)
*C08G 65/326* (2006.01)
*C08G 65/334* (2006.01)
*C08L 71/02* (2006.01)

(52) U.S. Cl.
CPC ............ *C08F 2/26* (2013.01); *C08F 2/30* (2013.01); *C08G 65/326* (2013.01); *C08G 65/3344* (2013.01); *C08L 71/02* (2013.01); *C08L 2205/02* (2013.01)

(58) Field of Classification Search
CPC .. C08G 65/3344; C08L 71/02; C08L 2205/02
USPC ............ 516/30, 58, 200; 510/535, 536, 537
See application file for complete search history.

(56) References Cited

U.S. PATENT DOCUMENTS

| | | | |
|---|---|---|---|
| 3,565,939 A | 2/1971 | Beiser | |
| 3,890,239 A | 6/1975 | Dycus et al. | |
| 4,285,356 A | 8/1981 | Sifferman | |
| 4,293,428 A | 10/1981 | Gale et al. | |
| 4,299,994 A | 11/1981 | Stahl | |
| 4,395,364 A | 7/1983 | Murata et al. | |
| 4,879,399 A | 11/1989 | Latella et al. | |
| 6,048,831 A | 4/2000 | Mori et al. | |
| 6,147,131 A | 11/2000 | Mork et al. | |
| 6,380,302 B1 | 4/2002 | Ikenaga et al. | |
| 6,506,715 B1 | 1/2003 | Schultz et al. | |
| 6,706,931 B2 | 3/2004 | Edwards | |
| 6,891,056 B2 | 5/2005 | Edwards et al. | |
| 7,833,518 B2 | 11/2010 | Sakuma et al. | |
| 7,906,474 B2 | 3/2011 | Varineau et al. | |
| 8,048,842 B2 | 11/2011 | Doi et al. | |
| 8,309,510 B2 | 11/2012 | Chiba et al. | |
| 8,828,364 B2 | 9/2014 | Gates et al. | |
| 8,877,702 B2 | 11/2014 | Nomura et al. | |
| 9,555,385 B2* | 1/2017 | Shen | C07C 305/10 |
| 2006/0148981 A1 | 7/2006 | Schmidt-Thummes et al. | |
| 2008/0207939 A1* | 8/2008 | Tropsch | A61K 8/463 |
| | | | 558/34 |
| 2010/0305254 A1* | 12/2010 | Ikenaga | C08F 2/26 |
| | | | 524/156 |
| 2011/0098492 A1 | 4/2011 | Varineau et al. | |
| 2011/0152425 A1 | 6/2011 | Tysak et al. | |
| 2011/0245131 A1* | 10/2011 | Mu | C11D 1/722 |
| | | | 510/351 |
| 2011/0266496 A1 | 11/2011 | Mitsuda et al. | |
| 2012/0115769 A1* | 5/2012 | Nomura | C11D 1/8305 |
| | | | 510/351 |
| 2015/0224462 A1 | 8/2015 | Shen et al. | |
| 2015/0367307 A1 | 12/2015 | Shen et al. | |
| 2017/0002296 A1* | 1/2017 | Shen | C11D 1/722 |

FOREIGN PATENT DOCUMENTS

| | | |
|---|---|---|
| CN | 101896506 | 11/2010 |
| CN | 102257111 | 11/2011 |
| JP | S5778937 | 5/1982 |
| JP | 1998036885 | 2/1998 |
| JP | 2000345191 | 12/2000 |
| JP | 2006232946 | 9/2006 |
| JP | 2006232947 | 9/2006 |
| JP | 2007077181 | 3/2007 |
| JP | 2010185063 | 3/2009 |
| WO | WO 2011/007891 A1 * | 1/2011 |
| WO | 2011110503 | 9/2011 |
| WO | 2012147915 | 11/2012 |

OTHER PUBLICATIONS

Derwent Abstract, week 201706, London: Derwent Publications Ltd., AN 2015-355524, Class A25, US 20170002296 A1, (Dow Global Technologies Inc), abstract.*

* cited by examiner

ANIONIC SURFACTANT COMPOSITIONS AND USE THEREOF

FIELD

This invention relates to a surfactant composition that is useful as an alternative to alkylphenol ethoxylates (APEs) as an emulsifier for emulsion polymerization. The surfactant composition contains an alkyl alkoxylate sulfate of the chemical structure described below.

BACKGROUND

Surfactants are broadly used as wetting agents in waterborne formulations. Alkylphenol ethoxylates (APEs) are widely recognized as good surfactants in a large variety of applications. APE surfactants, however, suffer from a poor public perception of their environmental compatibility. In addition, they are subject to increasing environmental regulation aimed at reducing their consumption in many applications, including in emulsion polymerization (EP). Therefore, the use of APE type surfactants is declining and suppliers are seeking to provide other surfactants to replace them.

Emulsion polymerization (EP) is a polymerization process in which poorly water soluble monomers are emulsified in water with the aid of emulsifiers and then polymerized with initiators. Surfactants play a key role in emulsion polymerization and in particular, APE based surfactants are generally considered the standard. However, in view of the issues with APE surfactants as discussed above, there is a need for new non-APE materials that exhibit properties suitable for emulsion polymerization. Such properties may include reduced foaming, emulsion formulation stability, and mechanical stability.

The problem addressed by this invention is the provision of new surfactants that are commercially viable alternatives for APE materials in emulsion polymerization.

STATEMENT OF INVENTION

We have now found that surfactant compositions as described herein exhibit a number of useful properties that are comparable to, and in some instances better than, properties observed with APE surfactants. Such properties include, for instance, one or more of good surface tension reduction, low foam and quick foam collapse, rapid wetting, and formulation stability. Advantageously, therefore, the surfactant compositions of the invention are viable alternatives to APE surfactants for emulsion polymerization.

In one aspect, there is provided a surfactant composition comprising an alkyl alkoxylate sulfate of formula I:

(I)

wherein $R^1$ is linear or branched $C_4$-$C_{10}$ alkyl; $R^2$ is $CH_3$ or $CH_3CH_2$; x is a real number from 1 to 11; y is a real number from 1 to 20; and M is an alkali metal or $NH_4$.

In another aspect, there is provided a surfactant composition comprising an alkyl alkoxylate sulfate of formula I, as described above, together with a nonionic alkyl alkoxylate of formula II:

(II)

wherein $R^1$ is linear or branched $C_4$-$C_{10}$ alkyl; $R^2$ is $CH_3$ or $CH_3CH_2$; x is a real number from 1 to 11; and y is a real number from 1 to 20.

In a further aspect, there is provided a method of using a surfactant composition as described herein as an emulsifier in an emulsion formulation.

DETAILED DESCRIPTION

Unless otherwise indicated, numeric ranges, for instance as in "from 2 to 10," are inclusive of the numbers defining the range (e.g., 2 and 10).

Unless otherwise indicated, ratios, percentages, parts, and the like are by weight.

As noted above, the invention provides a surfactant composition comprising an alkyl alkoxylate sulfate of formula I. The surfactant composition exhibits several useful properties, including one or more of good surface tension reduction, low foam and quick foam collapse, rapid wetting, and calcium ion stability. The advantageous properties render the surfactant composition suitable as an emulsifier for emulsion polymerization.

The alkyl alkoxylate sulfate is of the following formula I:

(I)

wherein $R^1$ is linear or branched $C_4$-$C_{10}$ alkyl; $R^2$ is $CH_3$ or $CH_3CH_2$; x is a real number from 1 to 11; y is a real number from 1 to 20; and M is an alkali metal or $NH_4$.

In some embodiments, $R^1$ in formula I is linear or branched $C_6$-$C_{10}$ alkyl, alternatively linear or branched $C_8$-$C_{10}$ alkyl. In some embodiments, $R^1$ is 2-ethylhexyl ($CH_3CH_2CH_2CH_2CH(CH_2CH_3)CH_2$—). In some embodiments, $R^1$ is 2-propylheptyl ($CH_3CH_2CH_2CH_2CH_2CH(CH_2CH_2CH_3)CH_2$—).

In some embodiments, $R^2$ in formula I is $CH_3$. In some embodiments, $R^2$ is $CH_3CH_2$.

In some embodiments, x in formula I is from 4 to 6.

In some embodiments, y in formula I is from 1 to 11, alternatively from 3 to 11.

In some embodiments, M in formula I is sodium, potassium, or ammonium. In some embodiments, M is sodium or ammonium.

In some embodiments, in addition to the alkyl alkoxylate sulfate of formula I, the surfactant composition of the invention also comprises a nonionic alkyl alkoxylate of formula II:

(II)

wherein $R^1$ is linear or branched $C_4$-$C_{10}$ alkyl; $R^2$ is $CH_3$ or $CH_3CH_2$; x is a real number from 1 to 11; and y is a real number from 1 to 20.

In some embodiments, $R^1$ in formula II is linear or branched $C_6$-$C_{10}$ alkyl, alternatively linear or branched $C_8$-$C_{10}$ alkyl. In some embodiments, $R^1$ is 2-ethylhexyl ($CH_3CH_2CH_2CH_2CH(CH_2CH_3)CH_2$—). In some embodiments, $R^1$ is 2-propylheptyl ($CH_3CH_2CH_2CH_2CH_2CH(CH_2CH_2CH_3)CH_2$—).

In some embodiments, $R^2$ in formula II is $CH_3$. In some embodiments, $R^2$ is $CH_3CH_2$.

In some embodiments, x in formula II is from 4 to 6.

In some embodiments, y in formula II is from 1 to 11, alternatively from 3 to 11.

When the nonionic alkyl alkoxylate of formula II is present in the surfactant composition, the groups $R^1$, $R^2$, x, and y in formula I and formula II may be the same or different. In some embodiments, the groups $R^1$, $R^2$, x, and y in formula I and formula II are the same.

In some embodiments, the surfactant composition of the invention comprises an alkyl alkoxylate sulfate of formula I and a nonionic alkyl alkoxylate of formula II, wherein the weight ratio of the alkyl alkoxylate sulfate of formula I to the nonionic alkyl alkoxylate of formula II is from 99:1 to 10:90. In some embodiments, the weight ratio is from 95:5 to 50:50, alternatively from 90:10 to 70:30.

In some embodiments, the surfactant composition of the invention further comprises water.

In some embodiments, the surfactant composition of the invention comprises an alkyl alkoxylate sulfate of formula I, a nonionic alkyl alkoxylate of formula II, and water. In some embodiments, the amount of the alkyl alkoxylate sulfate of formula I is from 20 to 70% by weight, preferably from 30 to 60% by weight; the amount of the alkoxylate of formula II is from 0.1 to 30% by weight, preferably from 0.1 to 10% by weight; and the amount of water is from 25 to 75% by weight, preferably from 40 to 70% by weight, based on the total weight of the alkyl alkoxylate sulfate of formula I, the nonionic alkyl alkoxylate of formula II, and the water.

The surfactant composition of the invention may comprise additional additives, such as other surfactants/emulsifiers, and other additives commonly use in emulsion polymerization. In some embodiments, the surfactant composition of the invention further comprises a nonionic surfactant of the formula III: $R^3O$—$(AO)_z$—H (III), wherein $R^3$ is linear or branched $C_6$-$C_{24}$ alkyl, AO at each occurrence is ethyleneoxy, propyleneoxy, butyleneoxy, or random or block mixtures thereof, and z is from 1 to 50.

The surfactant compositions of the invention exhibit good surface tension reduction, low foam and quick foam collapse, rapid wetting, and they provide formulation stability properties, including good $Ca^{2+}$ stability. $Ca^{2+}$ stability may be understood as the tolerance of an emulsion to electrolytes. In downstream application, numerous additives may be mixed with an emulsion, thus, a good $Ca^{2+}$ stability indicates a good formulation stability. As a result of these properties, the surfactant compositions are suitable for use as emulsifiers in emulsion polymerization and indeed may be used as replacements for traditional APE based emulsifiers.

The emulsions in which the surfactant compositions of the invention may be used as emulsifiers are typically aqueous emulsions or dispersions of polymers and/or copolymers which are normally obtainable by emulsion polymerization. There are no particular restrictions as to the nature of the polymers and copolymers in these formulations. Polymers or copolymers based on the following monomer units are preferred: acrylic acid, acrylates, butadiene, methacrylic acid, methacrylates, styrene, and vinyl acetate. Thus for instance in some embodiments an emulsion formulation according to the invention comprises a surfactant composition as described above (including all described embodiments thereof), water, and a monomer.

A person of ordinary skill in the art can readily determine the effective amount of the surfactant composition of the invention that should be used in an emulsion polymerization formulation, via a combination of general knowledge of the applicable field as well as routine experimentation where needed. For instance, in some embodiments, a quantity of from 0.01 to 10 phm (per hundred monomer) by active weight of the surfactant composition, alternatively from 0.1 to 5 phm by active weight of the surfactant composition, or alternatively from 0.2 to 3 phm by active weight of the surfactant composition, based on the total weight of monomers used in the emulsion polymerization, may be suitable.

Nonionic alkyl alkoxylates of formula II as described above may be purchased from commercial vendors or they may be prepared by those skilled in the art using literature techniques (see for instance U.S. Patent publication number 2011/0098492, which is incorporated herein by reference). In a typical procedure, a suitable alcohol or fatty acid alcohol is alkoxylated with alkylene oxide compounds. Alkoxylation processes may, for instance, be carried out in the presence of acidic or alkaline catalysts, or by using metal cyanide catalysts. Alkaline catalysts may include, for instance, hydroxides or alcoholates of sodium or potassium, including NaOH, KOH, sodium methoxide, potassium methoxide, sodium ethoxide and potassium ethoxide. Base catalysts are normally used in a concentration of from 0.05 percent to about 5 percent by weight, preferably about 0.1 percent to about 1 percent by weight based on starting material.

The addition of alkylene oxides may, for instance, be carried out in an autoclave under pressures from about 10 psig to about 200 psig, preferably from about 60 to about 100 psig. The temperature of alkoxylation may range from about 30° C. to about 200° C., preferably from about 100° C. to about 160° C. After completion of oxide feeds, the product is typically allowed to react until the residual oxide is less than about 10 ppm. After cooling the reactor to an appropriate temperature ranging from about 20° C. to 130° C., the residual catalyst may be left unneutralized, or neutralized with organic acids, such as acetic, propionic, or citric acid. Alternatively, the product may be neutralized with inorganic acids, such as phosphoric acid or carbon dioxide. Residual catalyst may also be removed using ion exchange or an adsorption media, such as diatomaceous earth.

Alkyl alkoxylates sulfate of formula I may be prepared by sulfation of nonionic alkyl alkoxylates of formula II. For instance, the Chemithon sulfation process via sulfur trioxide is a sulfation process well known to those skilled in the art. Typically, pre-heated nonionic alkyl alkoxylate (40° C.) may be first contacted with an air-diluted sulfur trioxide in a continuous thin-film reactor, resulting in a quick and exothermic reaction. The crude sulfuric ester acid may be collected at about 55° C. A prompt neutralization by NaOH or $NH_4OH$ to transform sulfuric ester acid to sulfate salt is advantageous to avoid dark color formation and to reduce formation of impurities. Precise control of the molar ration of $SO_3$ to nonionic alkyl alkoxylate is preferred in order to produce high quality alkyl alkoxylate sulfate.

Some embodiments of the invention will now be described in detail in the following Examples.

EXAMPLES

Materials used in the examples include the following:

"Alkyl alkoxylate sulfate" means 2-ethylhexyl-O—$(CH_2CH(CH_3)$—$O)_{5.5}$—$(CH_2CH_2O)_3$—$SO_3NH_4$.

"Nonionic alkyl alkoxylate 1" means 2-ethylhexyl-O—$(CH_2CH(CH_3)$—$O)_{5.5}$—$(CH_2CH_2O)_3$—H.

"Nonionic alkyl alkoxylate 2" means 2-ethylhexyl-O—$(CH_2CH(CH_3)$—$O)_{5.5}$—$(CH_2CH_2O)_9$—H.

"APE Sulfate" means nonylphenol-(EO)4 Sulfate (an APE material) available from Rhodia as RHODAPEX® CO-436 (comparative material).

"APE-free sulfate" means a C12-14 alcohol(EO)4 sulfate available from Cognis as DISPONIL® FES-32 (comparative material).

Nonylphenol Ethoxylate: An APE material available from The Dow Chemical Company.

Example 1

Several alkyl alkoxylate sulfate compositions were prepared, including both sodium salt and ammonium salt. Lab-scale samples were prepared based on Chemithon sulfation process. The $SO_3$ was diluted with air to the ratio at 3.5% vol., then, reacted with pre-heated nonionic alkyl alkoxylate surfactants (at 40° C.) in a falling thin film reactor (length 2 m). Molar ratio of $SO_3$ to nonionic alkyl alkoxylate was maintained in the range of 0.98-1.0 by adjustment of the flowrate of nonionic alkyl alkoxylate (3-5 kg/h) to the reactor. Cooling water system was applied in the thin film reactor and the temperature in the ether sulfuric acid tank was measured around 55° C., followed with a prompt neutralization by NaOH or ammonia water with stirring.

Formation of the desired compound was confirmed by NMR. The $^{13}C$ NMR spectrum showed the disappearance of —$CH_2OH$ carbon at the chemical shift at δ=62.0 ppm and the presence of —$CH_2OSO_3^-$ carbon at δ=68.0 ppm, which indicated the high conversion of nonionic alkyl alkoxylate to alkyl alkoxylate sulfate.

The Table 1 shows some analytical date of these samples.

TABLE 1

| | Sample 1 ($NH_4^+$) | Sample 2 ($NH_4^+$) | Sample 3($Na^+$) |
|---|---|---|---|
| Formula I (% wt.) | 31.09 | 72.73 | 32.44 |
| pH | 7.4 | 8.0 | 8.3 |

Example 2

Property Testing

Various properties of inventive and comparative compositions are shown in Table 2.

TABLE 2

| | Alkyl alkoxylate sulfate (inventive) | Alkyl alkoxylate sulfate + Nonionic alkyl alkoxylate 1 (90:10 by wt) (inventive) | APE Sulfate (comparative) | APE-free sulfate (comparative) |
|---|---|---|---|---|
| Active content (%) | 50 | 50 | 58-60 | 30-32 |
| Appearance (20° C.) (visual measurement) | clear, pale yellow | clear, pale yellow | clear, pale yellow | clear, pale yellow |
| Surface Tension at CMC (mN/m, 20° C.)[1] | 35 | 32 | 34 | 42 |
| CMC (ppm) (Based on Surface Tension measurement) | 3000 | 2000 | 300 | 125 |
| Foam Height (Ross Miles, 0/5 min at 0.2%)[2] | 108/24 | 93/17 | 106/102 | 113/112 |
| Draves wetting (s)[3] | 5.3 +/− 0.5 | 3.0 +/− 0.4 | 5.9 +/− 0.4 | 263.0 +/− 32.9 |
| $Ca^{2+}$ stability (CaCl2, 1% Surfactant)[4] | 10-15% wt. | 10-15% wt. | <2.5% wt. | ≈15% wt. |
| Anti-alkaline (NaOH, 1% surfactant)5 | 5-10% wt. | 5-10% wt. | <2.5% wt. | 10-15% wt. |
| Viscosity (cP, at 20° C. & 60 rpm, #62 probe) | 245 | 202 | 120.5 | 63.5 |

[1]Measured according to standard GB/T-5549-2010;
[2]by GB/T 7462-94 standard;
[3]by GB/T 11983-2008 standard;
[4]by GB/T 7381-2010;
5by GB/T 5556-2003 standard.

As is apparent from Table 2, in comparison with APE sulfate or APE-free sulfate, the inventive compositions showed various useful properties. For instance, the alkyl alkoxylate sulfate +nonionic alkyl alkoxylate 1 composition exhibited surface tension at 32 mN/m, lower than APE sulfate and APE-free sulfate. Both inventive compositions showed low foam, and quick foam collapse, properties, in contrast to both the APE sulfate and APE-free sulfate compositions, which have almost no foam collapse property. Both inventive compositions showed quick wetting property, which was lower than the APE-free sulfate.

Example 3

Emulsion Polymerization

Basic Formula of Styrene-Butyl Acrylate Emulsion:

Monomers include: butyl acrylate, styrene, acrylamide and acrylic acid;

Initiator is ammonium persulfate;
Glass transition temperature (Tg): 23° C.;
Anionic surfactants: 0.51 phm (per hundred monomer); non-ionic surfactants: 0.54 phm.

Basic Formulation of Pure Acrylate Emulsion:
Monomers include: acrylic acid, butyl acrylate, methacrylic acid;
Glass transition temperature (Tg): 10° C.;
Anionic surfactants: 1.0 phm.

Basic Polymerization Procedure of Styrene-Butyl Acrylate Emulsion:

Pre-emulsify the alkyl alkoxylate sulfate composition with sodium bicarbonate, water and above mentioned monomers. Add the second part of surfactant composition and water into the reactor; start heating to a temperature in the range of 80-90° C.; then, add the first part of ammonium persulfate. Start dropwise addition of pre-emulsion with the second part of ammonium persulfate during 3 h. After addition, keep at the same temperature for 1 h; an emulsion polymerization is performed. After cooling down to room temperature and pH adjustment by aqueous ammonia to neutral 40° C., the polymer emulsion is obtained.

Preparation of other Emulsions:

For the other emulsions preparation, the procedure described above is followed. Emulsifier composition is changed. See the below Table 3 for the emulsifier details of other emulsions.

TABLE 3

Details of emulsion preparation

| Example Type | Emulsion | Emulsion type | Surfactant composition | +Non-ionic |
|---|---|---|---|---|
| Inventive | 1 | St-Acrylate | alkyl alkoxylate sulfate | — |
| Comparative | 2 | St-Acrylate | APE sulfate | — |
| Inventive | 3 | St-Acrylate | alkyl alkoxylate sulfate | Nonylphenol Ethoxylate |
| Comparative | 4 | St-Acrylate | APE sulfate | Nonylphenol Ethoxylate |
| Comparative | 5 | St-Acrylate | APE-free sulfate | Nonylphenol Ethoxylate |
| Inventive | 6 | St-Acrylate | alkyl alkoxylate sulfate | nonionic alkyl alkoxylate 2 |
| Comparative | 4 | St-Acrylate | APE sulfate | Nonylphenol Ethoxylate |
| Inventive | 7 | Pure-Acrylate | alkyl alkoxylate sulfate | — |
| Comparative | 8 | Pure-Acrylate | APE-free sulfate | — |

Foaming Property

The emulsion is diluted to 1% by weight of its solid content. Then, 250 mL of diluted emulsion are poured into a test tube. Air-bubble (air-flow at 1.8 L/s) the aqueous emulsion solution for 1 min; stop air-bubbling and record the foam heights in the next 5 min. Foam test results are shown in FIGS. 1-4.

Figure 1:
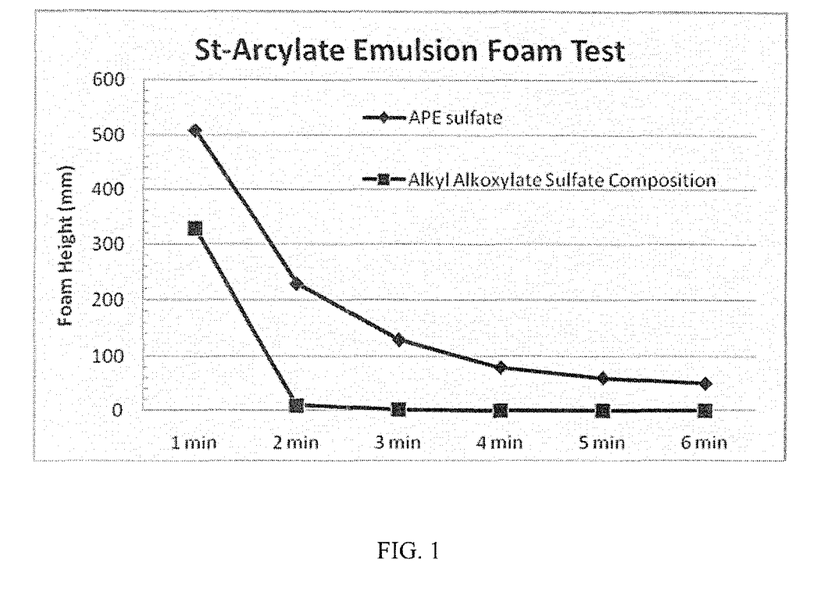
FIG. 1 is plot showing foaming properties for an inventive emulsion according to one embodiment of the invention (Emulsion 1) and a comparative emulsion (Emulsion 2).

FIG. 1 compares inventive Emulsion 1 (see Table 3) and comparative Emulsion 2. As is apparent, the inventive emulsion exhibited improved low foam and quick foam collapse property relative to the comparative emulsion.

Figure 2:
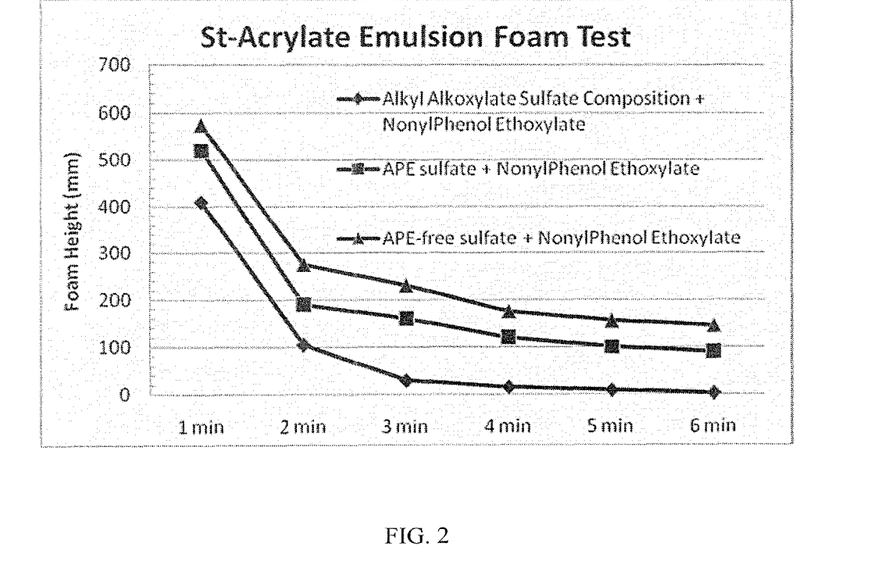
FIG. 2 is plot showing foaming properties for an inventive emulsion according to one embodiment of the invention (Emulsion 3) and comparative emulsions (Emulsions 4 and 5).

FIG. 2 compares foam properties for Emulsion 3 (inventive) and Emulsions 4 and 5 (comparative). Again, the inventive emulsion showed lower foam and fast foam collapse property.

Figure 3:
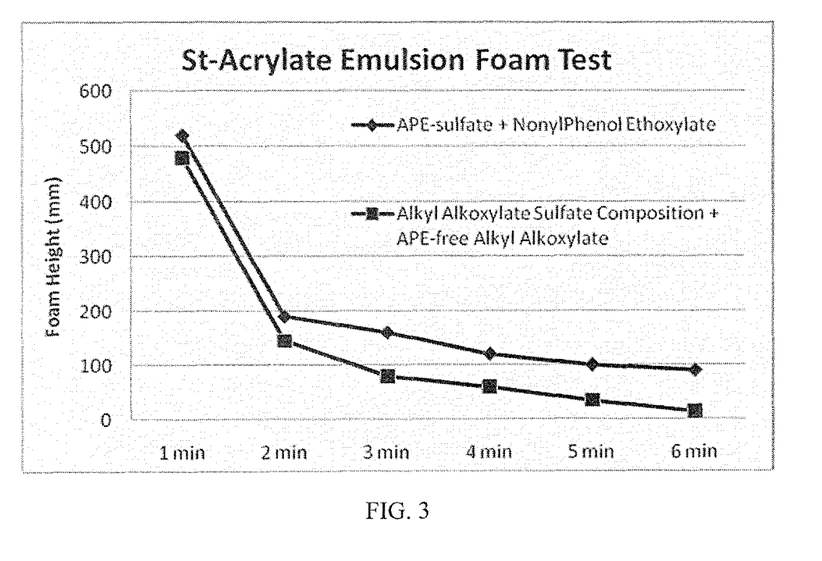
FIG. 3 is plot showing foaming properties for an inventive emulsion according to one embodiment of the invention (Emulsion 6) and a comparative emulsion (Emulsion 4).

FIG. 3 compares Emulsion 6 (inventive) and Emulsion 4 (comparative). Again, the inventive emulsion showed good low foam and quick foam collapse property.

Figure 4:
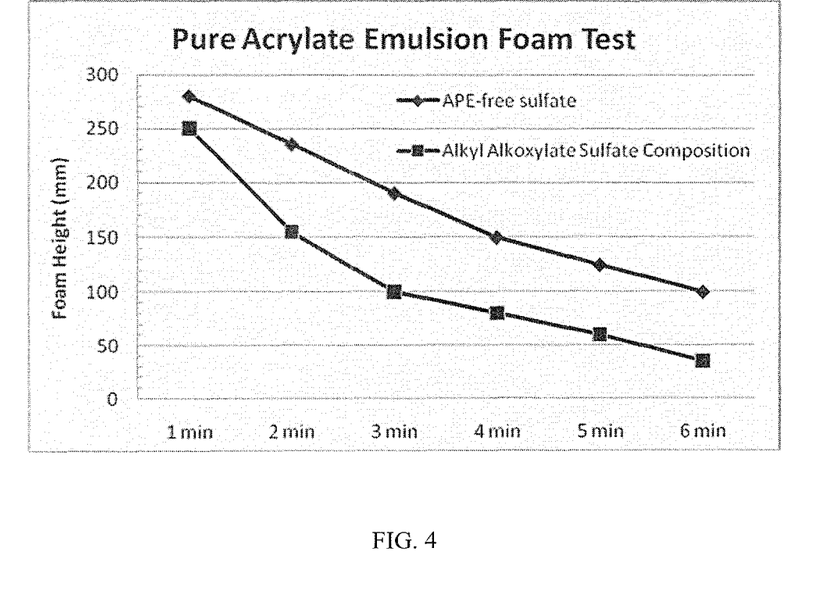
FIG. 4 is plot showing foaming properties for an inventive emulsion according to one embodiment of the invention (Emulsion 7) and a comparative emulsion (Emulsion 8).

FIG. 4 compares Emulsion 7 (inventive) and Emulsion 8 (comparative). Low foam and quick foam collapse are again observed with the inventive material.

$Ca^{2+}$ Stability

Test method: Add $CaCl_2$ aqueous solution (concentration at 5 or 10% wt.) into 20 ml of emulsion; store the $CaCl_2$ containing emulsion for 48 h at room temperature; any agglomeration or non-homogeneity present in the emulsion signifies poor $Ca^{2+}$ stability, consequently, failure in the $Ca^{2+}$ stability test. Test results are shown in Table 4.

TABLE 4

$Ca^{2+}$ stability

| | Example Type | Emulsion & Type | | Surfactants | $Ca^{2+}$ stability |
|---|---|---|---|---|---|
| Comparison 1 | Inventive | 1 | St-Acrylate | alkyl alkoxylate sulfate | Fail with 10 mL of $CaCl_2$ aq (5%) |

TABLE 4-continued

Ca²⁺ stability

| | Example Type | Emulsion & Type | | Surfactants | Ca²⁺ stability |
|---|---|---|---|---|---|
| | Comparative | 2 | St-Acrylate | APE sulfate | Fail with 4 mL of CaCl$_2$ aq (5%) |
| Comparison 2 | Inventive | 3 | St-Acrylate | alkyl alkoxylate sulfate + nonylphenol ethoxylate | Pass with 20 mL of CaCl$_2$ aq (10%) |
| | Comparative | 4 | St-Acrylate | APE sulfate + nonylphenol ethoxylate | Fail with 4 mL of CaCl$_2$ aq (5%) |
| | Comparative | 5 | St-Acrylate | APE-free sulfate + nonylphenol ethoxylate | Fail with 4 mL of CaCl$_2$ aq (5%) |
| Comparison 3 | Inventive | 6 | St-Acrylate | alkyl alkoxylate sulfate + nonionic alkyl alkoxylate 2 | Pass with 20 mL of CaCl$_2$ aq (10%) |
| | Comparative | 4 | St-Acrylate | APE sulfate + nonylphenol ethoxylate | Fail with 4 mL of CaCl$_2$ aq (5%) |
| Comparison 4 | Inventive | 7 | Pure-Acrylate | alkyl alkoxylate sulfate | Fail with 10 mL of CaCl$_2$ aq (10%) |
| | Comparative | 8 | Pure-Acrylate | APE-free sulfate | Fail with 10 mL of CaCl$_2$ aq (5%) |

In Table 4, the comparison 1 shows that in St-Acrylate emulsion, when no non-ionic surfactant is added as emulsifier, the emulsion with alkyl alkoxylate sulfate as emulsifier demonstrated better Ca²⁺ stability than the one with APE sulfate. In the comparison 2, when the same non-ionic surfactant (nonylphenol ethoxylate) was added in the surfactant composition in St-Acrylate emulsion, the emulsion with alkyl alkoxylate sulfate as emulsifier had better Ca²⁺ stability than both others with APE sulfate and APE-free sulfate in the surfactant composition.

In the comparison 3, the comparison between alkyl alkoxylate sulfate composition and classic APE surfactant composition in St-Acrylate emulsion was made. Alkyl alkoxylate sulfate offered not only an eco-friendly profile but also better performance on Ca²⁺ stability.

In the comparison 4, no non-ionic emulsifier was used in the Pure Acrylate emulsion. Alkyl alkoxylate sulfate provided also an improved Ca²⁺ stability.

What is claimed is:

1. A surfactant composition comprising an alkyl alkoxylate sulfate of formula I:

wherein R¹ is linear or branched C$_4$-C$_{10}$ alkyl;
R² is CH$_3$ or CH$_3$CH$_2$;
x is a real number from 1 to 11;
y is a real number from 1 to 20; and
M is an alkali metal or NH$_4$; the surfactant composition further comprising a nonionic alkyl alkoxylate of formula II:

wherein R¹ is linear or branched C$_4$-C$_{10}$ alkyl;
R² is CH$_3$ or CH$_3$CH$_2$;
x is a real number from 1 to 11; and
y is a real number from 1 to 20.

2. The surfactant composition of claim 1 further comprising water, and wherein the amount of the alkyl alkoxylate sulfate of formula I is from 20 to 70% by weight, the amount of the nonionic alkyl alkoxylate of formula II is from 1 to 30% by weight, and the amount of water is from 25 to 75% by weight, based on the total weight of the anionic alkoxylate of formula I, the nonionic alkyl alkoxylate of formula II, and the water.

3. The surfactant composition of claim 1 or 2 wherein R¹ in formula I and formula II is independently linear or branched C$_6$-C$_{10}$ alkyl.

4. The surfactant composition of claim 1, wherein R¹ in formula I and formula II is independently 2-ethylhexyl or 2-propylheptyl.

5. The surfactant composition of claim 1, wherein x in formula I and formula II is independently from 4 to 6.

6. The surfactant composition of claim 1, wherein y in formula I and formula II is independently from 1 to 11.

7. The surfactant composition of claim 1, that is present in an emulsion polymerization formulation.

8. A method of use of the surfactant composition of claim 1, comprising:
forming a styrene-butyl acrylate emulsion; and
adding the surfactant composition of claim 1 to the styrene-butyl acrylate emulsion as an emulsifier for emulsion polymerization.

\* \* \* \* \*